United States Patent
Gupta et al.

(10) Patent No.: US 9,655,866 B2
(45) Date of Patent: May 23, 2017

(54) MILD ANTIBACTERIAL CLEANSING COMPOSITIONS

(71) Applicant: Conopco, Inc., Englewood Cliffs, NJ (US)

(72) Inventors: Shashank Narendra Gupta, Uttar Pradesh (IN); Nitish Kumar, Bihar (IN); Gagarin Wamanrao Raikar, Mumbai (IN); Rajan Raghavachari, Mumbai (IN); Vibhav Ramrao Sanzgiri, Mumbai (IN)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 14/442,783

(22) PCT Filed: Nov. 13, 2013

(86) PCT No.: PCT/EP2013/073690
§ 371 (c)(1),
(2) Date: May 14, 2015

(87) PCT Pub. No.: WO2014/082854
PCT Pub. Date: Jun. 5, 2014

(65) Prior Publication Data
US 2015/0306044 A1   Oct. 29, 2015

(30) Foreign Application Priority Data

Nov. 29, 2012 (IN) .................. 3398/MUM/2012
Jan. 11, 2013 (EP) ..................... 13150941

(51) Int. Cl.
| A61K 31/05 | (2006.01) |
| A61K 8/34 | (2006.01) |
| A61K 8/44 | (2006.01) |
| A61Q 17/00 | (2006.01) |
| A61Q 19/10 | (2006.01) |
| A61K 31/045 | (2006.01) |

(52) U.S. Cl.
CPC ............... *A61K 31/05* (2013.01); *A61K 8/34* (2013.01); *A61K 8/347* (2013.01); *A61K 8/44* (2013.01); *A61K 8/442* (2013.01); *A61K 31/045* (2013.01); *A61Q 17/005* (2013.01); *A61Q 19/10* (2013.01)

(58) Field of Classification Search
CPC ........ A61K 31/05; A61K 31/045; A61K 8/44; A61K 8/347; A61K 8/442; A61K 8/34; A61Q 19/10; A61Q 17/005
See application file for complete search history.

(56) References Cited

U.S. PATENT DOCUMENTS

| 6,146,622 A | 11/2000 | Castillo |
| 2007/0212304 A1* | 9/2007 | Goldberg ........... A61K 49/0006 424/9.6 |
| 2011/0245126 A1 | 10/2011 | Tsaur |

FOREIGN PATENT DOCUMENTS

| WO | WO9218100 | 10/1992 |
| WO | WO9532705 | 12/1995 |
| WO | WO9721795 | 6/1997 |
| WO | WO2010046238 | 4/2010 |
| WO | WO2011120780 | 10/2011 |
| WO | WO2011138179 | 11/2011 |
| WO | WO2012022614 | 2/2012 |
| WO | WO2013083581 | 6/2013 |
| WO | WO2013083582 | 6/2013 |
| WO | WO2013083583 | 6/2013 |
| WO | WO2013083584 | 6/2013 |
| WO | WO2013083590 | 6/2013 |
| WO | WO2013083592 | 6/2013 |
| WO | WO2013083593 | 6/2013 |
| WO | WO2013083594 | 6/2013 |
| WO | WO2013083595 | 6/2013 |

OTHER PUBLICATIONS

Search Report in EP13150941 dated Jul. 10, 2013. pp. 1 to.
Search Report in PCTEP2013073690 dated Jun. 23, 2014. pp. 5 to 9.
Written Opinion 2 in PCTEP2013073690 dated Jan. 15, 2015. pp. 10 to 18.
Written Opinion in EP13150941 dated Jul. 10, 2013. pp. 19 to 22.
Written Opinion1 in PCTEP2013073690 dated Jun. 23, 2014. pp. 23 to 29.
IPRP in PCT/EP2013/073690 dated Apr. 21, 2015. pp. 30 to 45.

* cited by examiner

*Primary Examiner* — Sudhakar Katakam

(74) *Attorney, Agent, or Firm* — Ronald A. Koatz

(57) ABSTRACT

Disclosed is a cleansing composition comprising: (i) a non-soap surfactant which is an alkyi glycinate, alkyi carboxy glycinate, sarcosinate, glutamate or a mixture thereof; and, (ii) one or more antimicrobial agent, wherein pH of said composition is at least 8.5 and zein number of said composition is in the range of 10 to 65 and wherein soap content of said composition is not greater than 5 wt %. The formulation is highly alkaline, yet gives mild antibacterial cleansing action.

8 Claims, No Drawings

MILD ANTIBACTERIAL CLEANSING COMPOSITIONS

FIELD OF THE INVENTION

The invention relates to mild antibacterial cleansing compositions, particularly to personal cleansing compositions.

BACKGROUND OF THE INVENTION

Personal cleansing compositions are available in wide ranging product formats e.g. from soap bars, liquid soap, body-wash compositions and self-foaming compositions to shampoos. Sometimes such cleansing compositions are also included in cleansing wipes.

Personal cleansing compositions are formulated for specific purpose, such as antibacterial effect and exfoliation to mild and gentle cleansing.

Usually the pH of mild cleansing compositions is close to or less than 7. Even if the pH of such compositions is alkaline, it is usually below 8. The reason is that generally strongly alkaline cleansers such as conventional bars of soap and soap-containing liquid cleaners are considered to be harsh. On the other hand, conventional SLES-CAPB based cleaning compositions having pH of about 5 to 7 are generally considered gentle and mild and therefore these surfactants form the base of many such compositions.

There is a growing demand for mild liquid cleansing formulations which additionally have an antibacterial effect. Antibacterial cleansers are preferred because they kill germs and mild personal cleansers are preferred as their use leads to minimal skin irritation and dryness. However, the combination of mild cleansing formulations and strong antibacterial effect is difficult to achieve.

Thus, for example, while soaps provide antibacterial effects, they are not mild to the skin. When very mild non-soap surfactants are used, antibacterial effect is greatly compromised due to the requirement to formulate them around neutral pH for better performance.

The balancing act between providing mildness and effective antibacterial effectiveness is recognized for example in International Publication WO 92/18100 A1. In this publication, improved clinical mildness is said to be provided through the use of a water soluble cationic polymer. Cationic polymer is apparently used instead of additional ethoxylated surfactant because the percent of ethoxylated mildness surfactant must be minimized in order not to affect antibacterial effectiveness.

It can be readily seen that there is a technical problem to provide effective antibacterial action in the presence of very mild surfactants.

WO9532705 A1 (Unilever) discloses mild antibacterial cleansers but their pH is in the acidic range.

WO2011138179A1 (Unilever) discloses a mild cleansing composition having specific mild surfactant system with good foam and phase stability. The surfactant system includes alkanoyl glycinates and amphoacetate surfactants. The composition also includes emollients for good foaming and mildness. The pH of the compositions is less than 8.

WO2012/022614A1 discloses mild isotropic liquid compositions having specific surfactant system which includes glycinates, amphoteric surfactants and alkyl sulfates and the pH of the resultant compositions is in the narrow range of 6.5 to 7.5. The associative acrylate polymer provides interalia, mildness.

Antibacterial personal cleansing compositions (particularly soap bars or soap based liquid cleansers) usually contain 2,4,4'-trichloro-2'-hydroxydiphenyl ether (TRICLOSAN®) or trichlorocarbanilide (TCC) or p-chloro-m-xylenol as the active antibacterial agent. Usually the pH of such compositions is 9 to 10. While there are personal cleansing compositions (largely containing synthetic non-soap surfactants as explained earlier) which are neutral or low pH, however such compositions are generally not found to be effective against some bacteria particularly relevant for hand hygiene e.g., $E.\ coli$.

WO10046238 A1 (Unilever) discloses cleansing compositions comprising thymol and terpineol in selective proportions to provide fast antimicrobial action.

WO11120780 A1 (Unilever) discloses super mild surfactant systems used in combination with skin or hair benefit agent(s). Disclosed surfactant systems have a combination of specific alkanoyls or mixtures of alkanoyl surfactants with specifically identified fatty acyl isethionate product to provide synergy which reduces irritation (as measured by Patch Testing).

WO9721795 A1 (Unilever) discloses cleaning composition of pH<6 or pH>8 which include ethoxylated nonionic surfactant of HLB of 10-14, a C1-C5 linear or branched alcohol. The use of 1 to 30 wt % of alcohol greatly improves the biocidal properties.

U.S. Pat. No. 6,146,622 A (Alcon Labs) discloses use of anionic amino acid based surfactants to enhance antimicrobial effectiveness in topically administrable pharmaceutical compositions containing at least one active ingredient.

Therefore, cleansing compositions which show antibacterial action but which at the same time are mild and gentle to the skin are generally difficult to formulate.

We have now been able to formulate highly alkaline, yet highly mild antibacterial cleansing compositions.

No attempt known to the applicant herein has ever been made to provide a composition having the stated seemingly opposite properties as it is inherently against the teachings of known art in view of the apprehended adverse impact on mildness. On the other hand, it is equally against the suggestions of known art to include an antibacterial agent in a mild and gentle personal cleansing composition because pH of such compositions is generally acidic.

SUMMARY OF THE INVENTION

In a first aspect disclosed herein is a cleansing composition comprising:
(i) a non-soap surfactant which is an alkyl glycinate, alkyl carboxy glycinate, sarcosinate, glutamate or a mixture thereof; and,
(ii) one or more antimicrobial agent,
wherein pH of said composition is at least 8.5 and zein number of said composition is in the range of 10 to 65 and wherein soap content of said composition is not greater than 5 wt %.

These and other aspects features and advantages will become apparent to those of ordinary skill in the art from a reading of the following detailed description and the appended claims.

DETAILED DESCRIPTION OF THE INVENTION

In a first aspect disclosed herein is a cleansing composition comprising:
(i) a non-soap surfactant which is an alkyl glycinate, alkyl carboxy glycinate, sarcosinate, glutamate or a mixture thereof; and, (ii) one or more antimicrobial agent,
wherein pH of said composition is at least 8.5 and zein number of said composition is in the range of 10 to 65 and wherein soap content of said composition is not greater than 5 wt %.

The Non-Soap Surfactant:

All cleansing compositions usually contain one or more surfactants. The surfactants provide basic cleansing action. Some surfactants are usually used in combination with each other, thereby constituting a "surfactant system". A well known example is that of SLES and CAPB. SLES is sodium lauryl ethoxy sulphate, an anionic surfactant and CAPB is coco amidopropyl betaine, a betaine type of surfactant.

The non-soap surfactant is an alkyl glycinate, alkyl carboxy glycinate, sarcosinate, glutamate or a mixture thereof.

The alkyl glycinates and the alkyl carboxy glycinates (also known as alkanoyl glycinates are generally used in the form of their salts. Preferred salts include alkali metal salts such as potassium/sodium salts or alkanolamino salts such as trialkanolamine salts.

As is well known in the art, alkanoyl is the systematic name for group:

which is also known as an acyl group. Thus, alkanoyl glycinate is the same as acyl glycinate (or alkyl carboxy glycinate) and represents a molecule, for example, where salt of acyl group, such as for example:

(where R may be, for example, $C_8$-$C_{24}$, preferably $C_{12}$-$C_{20}$) is combined with glycine:

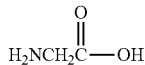

to form the alkanoyl glycinate (an amide where alkanoyl group bonds to nitrogen to form amide):

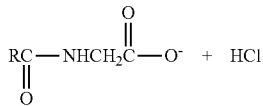

The above reaction may be conducted, for example, by an acid chloride route where R group on the acyl chloride is used to define the R group on the final alkanoyl glycinate (e.g., cocoyl glycinate if R in the acyl group is a cocoyl group).

Preferred compositions include 1 to 20 wt % of the alkyl glycinate or alkyl carboxy glycinate. The wt % of alkyl glycinate or alkyl carboxy glycinate will largely depend on the format of the cleansing composition, e.g., a thick viscous product like a shampoo will have more of the alkyl glycinate or alkyl carboxy glycinate surfactant. On the other hand, an aqueous and dilute composition such a self-foaming composition which is usually packaged in a suitable dispenser which allows for entrainment of air, preferably contains up to 8 wt % of the alkyl glycinate or alkyl carboxy glycinate.

Where the alkyl glycinate or alkyl carboxy glycinate is present in the composition, it serves the primary role of cleansing.

Sarcosinates are generally indicated by the formula: $R_1CON(CH_3)CH_2CO_2M$, where R1 ranges from $C_8$-$C_{20}$ alkyl and M is a solubilizing cation.

The preferred glutamate surfactants are N-acyl glutamates.

Preferred compositions include 1 to 20 wt % of the sarcosinate or the glutamate surfactants.

Co-Surfactant

Preferred compositions also include 1 to 15 wt %, more preferably 2 to 4 wt % salts of amphoacetates. Amphoacetates are desirable surfactants because they help cleanse and are milder than anionic surfactants (they are, for example, amphoteric), but they typically don't foam as well as the anionic surfactants. A combination of amphoacetate and alkanoyl glycinate surfactant foams better than a combination of amphoacetates with other surfactants such as sodium lauryl ether sulfate.

The soap (alkali metal salts of carboxylic acid) content of the composition is not greater than 5 wt %, preferably less than 3 wt % and most preferably less than 1 wt %. Without wishing to be bound by theory it is believed that the presence of soap affects clarity of the compositions so it is preferred to keep the soap content to a minimum. Without wishing to be bound by theory it is believed that soaps crystallize at lower temperatures. Therefore, a greater content of soaps might adversely affect the transparency of the resultant compositions particularly at lower temperature. Further, the soap content that can be safely included in the disclosed compositions is limited because soaps are also believed to affect viscosity and visual appearance of the compositions. If at all any soap is included in the compositions, it is usually partly replace the glycinate surfactants so that raw material costs can be minimised. A further belief is that glycinate surfactants contain some residual glycine which crystallizes at lower pH but which solubilises at higher pH. Further, clear (i.e. non-turbid) compositions also connote mildness.

Antibacterial Activity and Antimicrobial Agent

The cleansing compositions include an antimicrobial agent which preferably is an antibacterial agent. The agent is primarily responsible for antibacterial action. Suitable antibacterial agents include 2-hydroxy-4,2',4'-trichlorodiphenylether (DP300); 2,6-dimethyl-4-hydroxychlorobenzene (PCMX); 3,4,4'-trichlorocarbanilide (TCC); 3-trifluoromethyl-4,4'-dichlorocarbaniide (TFC); 2,2'-dihydroxy-3,3',5,5',6,6'-hexachlorophenylmethane; 2,2'-dihydroxy-3,3',5,5'-tetrachlorodiphenylmethane; 2,2'-dihydroxy-3,3',dibromo-5,5'-dichlorodiphenylmethane; 2-hydroxy-4,4'-dichlorodiphenylether; 2-hydroxy-3,5',4-tribromodiphenlyether; and 1-hydroxyl-4-methyl-6-(2,4,4-trimethylpentyl)-2(1H)-pyridinone (Octopirox), thymol and terpeniol. Particularly preferred antibacterial agents are thymol and terpeniol, optimally used in combination. In preferred compositions, the content of thymol ranges from 0.05 to 5 wt %, more preferably 0.1 to 1 wt % and most preferably 0.1 to 0.4 wt %. Above the preferred range, the compositions may have strong smell, which may not be preferred by some consumers. However, suitable strong masking agents liked perfumes can be used to mask the strong odour of thymol or terpeniol. As an alternative to thymol; thyme oil or thyme extract may also be added. Thyme oil or thyme extract is obtained from the thyme plant. Thyme plant refers to a plant belonging be genus *Thymus* and includes but is not limited to *Thymus vulgaris, Thymus zygis, Thymus satureoides, Thymus mastichina, Thymus broussonetti, Thymus maroccanus, Thymus pallidus, Thymus algeriensis, Thymus serpyllum, Thymus pulegoide,* and *Thymus citriodorus.*

Skin hygiene is of high priority to present day consumers. Consumers all over the world use various kinds of skin hygiene compositions.

Skin generally contains several different micro-organisms in concentrations exceeding millions or even billions of colony forming units (cfu) per square centimeter ($cm^2$). Many of these micro organisms are harmless, but there are also various pathogenic types or sub-species present, such as *Escherichia coli*, also referred to a *E. coli,* and *Staphylococcus aureus*, also referred to as *S. aureus.* Several other bacteria can be found in the skin flora, such as *Staphylococcus epidermidis*, also referred to as *S. epidermidis*, which is generally non-pathogenic, but is thought to be causing unpleasant body odour. Therefore present day consumers prefer cleansing products, especially skin cleansing products that can provide antimicrobial action.

Sanitizing and disinfecting soap compositions comprising chlorine-based antimicrobial agent such as triclosan require rather long contact time to provide antimicrobial action. In practice, users, in particular children, do not spend long time in cleaning and as a result, cleaning with such compositions does not provide adequate prevention from surface or topical infection or adequate protection against diseases. The user, in spite of cleaning hands, is likely to have skin with relatively inadequate bacterial removal and may cause contamination of further animate and/or inanimate surfaces and lead to spreading of pathogens and consequent diseases. Users in general and children in particular who wash contaminated hands before meals with slow-acting antimicrobial compositions for relatively short time are at risk of contacting diseases.

The efficacy of anti-bacterial activity of skin cleansing products containing bacteriostatic agents, however, can be measured in a variety of ways.

The efficacy of anti-bacterial activity of skin cleansing products containing bacteriostatic agents is generally measured in two types of assays. The first type measures the effect of anti-bacterial agents deposited on skin and is thus reflective of substantive effects. The second type measures the ability of the formulation to cause quick kill (less than 1 minute) of bacteria as determine by in-vitro solution tests.

The time of contact of bacteria with the cleanser in the invitro, short time kill assay is somewhat reflective of cursory wash conditions. In fact, a cursory wash may take much less than one minute.

Since many or most people who wash with soap bars may not use the bar for longer than a few seconds (the average wash time for children may be 10 seconds or less), it becomes apparent that there is a need to deliver anti-bacterial activity in a short period of time (e.g., 60 seconds or less, preferably 30 seconds or less) and, therefore, ways for reassuring quick-kill effect on bacteria are quite critical.

Therefore, people prefer compositions that give more efficacious antimicrobial action in a short period, preferably lesser than 2 minutes and in many cases less than one minute or sometimes as low as 15 seconds.

Preferred antimicrobial compositions include 0.05 to 5 wt % terpineol, more preferably 0.1 to 1 wt %, and most preferably 0.4 to 0.6 wt % terpineol. Most of the useful fast acting antimicrobial compositions have terpineol higher than 0.05 wt %, but lesser than 1 wt %. Below the preferred range, the kinetics of microbial kill was lower. Above the preferred range, the compositions were found to have strong smell, which may not be preferable to some consumers. Terpineol is preferably selected from alpha-terpineol, beta-terpineol, gamma-terpineol or mixtures thereof, alpha-terpineol being particularly preferred. Terpineol may be added to the antimicrobial compositions in purified form.

As an alternative to terpeniol, pine oil, which includes terpineol, may also be added to the mild personal cleansing compositions.

The reason for preference of a combination of thymol and terpeniol is that compositions having selective proportions of thymol and terpineol provide faster antimicrobial action.

The pH

The pH of the compositions is at least 8.5. Further preferably the pH is 9.5 to 11. It is believed that at pH below 8.5 the antimicrobial action is not rapid. The pH of the compositions is measured at a standard temperature of 25° C. Higher pH is important from two angles. In the first aspect, higher pH allows for formulation of transparent compositions. This is mainly driven by conversion of free glycine (where glycinate or alkanoyl glycinates are present) or fatty acids to corresponding more soluble salt forms which otherwise crystallize at lower temperature to make the formulation look hazy. Without wishing to be bound by theory it is believed that at higher pH some antibacterial agents become more soluble which increases their activity. Typical of such antibacterial agents are believed to be thymol and terpeniol.

Mildness-Test for Zein Number

Personal cleansing products are frequently marketed based on their degree of mildness to the skin of the user. Unfortunately, many surfactants in common use tend to bind to the skin proteins, which can result in irritation. Moreover different surfactants bind to skin proteins to varying degrees. Cleansers that do not leave residual surfactants on the skin are therefore more desirable for use.

The purpose of the Zein test is to investigate the irritation potential (harshness) of any cleansing composition which typically contains surfactants. Zein is a yellow corn protein which is similar to keratin and which is present in the skin and hair. Zein is denatured (solubilized) by irritant products (e.g., the surfactant product diluted in a specific amount of water). The more Zein dissolved by the solution, the higher is the predicted irritation potential. Conversely, mild compositions cause lesser dissolution of Zein. The Zein test provides a rapid and convenient screen for irritation potential, especially for compositions that contain surface active agents. The Zein number (also called Zein value) is a fairly standard parameter used by the cosmetics industry.

Other Preferred and Optional Ingredients

In addition to the disclosed ingredients, the preferred compositions will include one or more of the following ingredients.

Other Surfactants

Additional surfactants may be essential for more effective cleansing. They are compounds that have hydrophobic and hydrophilic portions that act to reduce the surface tension of the aqueous solutions they are dissolved in. Useful surfactants can include anionic, nonionic, amphoteric, and cationic surfactants, and blends thereof.

Anionic Surfactants

The cleansing compositions may contain one or more non-soap anionic surfactants. Non-soap anionic surfactants may preferably used at levels as low as 1 or 4, 8 or 12 wt %. and at levels as high as 16, 20 or 25 by wt %.

The anionic surfactant may be aliphatic sulfonates, such as a primary alkane (e.g., $C_8$-$C_{22}$) sulfonate, primary alkane (e.g., $C_8$-$C_{22}$) disulfonate, $C_8$-$C_{22}$ alkene sulfonate, $C_8$-$C_{22}$ hydroxyalkane sulfonate or alkyl glyceryl ether sulfonate (AGS); or aromatic sulfonates such as alkyl benzene sulfonate. The anionic may also be an alkyl sulfate (e.g., $C_{12}$-$C_{18}$ alkyl sulfate) or alkyl ether sulfate (including alkyl glyceryl ether sulfates). Among the alkyl ether sulfates are those having the formula:

where R is an alkyl or alkenyl having 8 to 18 carbons, preferably 12 to 18 carbons, n has an average value of greater than 1 preferably greater than 3; and M is a solubilizing cation such as sodium, potassium, ammonium or substituted ammonium. Ammonium and sodium lauryl ether sulfates are preferred.

The anionic may also be alkyl sulfosuccinates (including mono- and dialkyl, e.g., $C_6$-$C_{22}$ sulfosuccinates); alkyl and acyl taurates, alkyl and acyl sarcosinates, sulfoacetates, $C_6$-$C_{22}$ alkyl phosphates and phosphates, alkyl phosphate esters and alkoxyl alkyl phosphate esters, acyl lactates, $C_6$-$C_{22}$ monoalkyl succinates and maleates, sulphoacetates, alkyl glucosides and acyl isethionates, and the like.

Sulfosuccinates may be monoalkyl sulfosuccinates having the formula: $R_4O_2CCH_2CH(SO_3M)CO_2M$; and amide-MEA sulfosuccinates of the formula: $R_4CONHCH_2CH_2O_2CCH_2CH(SO_3M)CO_2M$ wherein $R_4$ ranges from $C_8$-$C_{22}$ alkyl and M is a solubilizing cation.

Taurates are generally identified by formula: $R_2CONR_3CH_2CH_2SO_3M$ where $R_2$ ranges from $C_8$-$C_{20}$ alkyl, $R_3$ ranges from $C_1$-$C_4$ alkyl and M is a solubilizing cation.

The cleansing composition may contain $C_8$-$C_{18}$ acyl isethionates. These esters are prepared by reaction between alkali metal isethionate with mixed aliphatic fatty acids having from 6 to 18 carbon atoms and an iodine value of less than 20. At least 75% of the mixed fatty acids have from 12 to 18 carbon atoms and up to 25% have from 6 to 10 carbon atoms.

One or more amphoteric surfactants may also be present in the composition. Amphoteric surfactants are preferably used at levels as low as 2, 4, or 6 wt % and at levels as high as 12, 16 or 20 wt %. Such surfactants include at least one acid group. This may be a carboxylic or a sulphonic acid group. They include quaternary nitrogen and therefore are quaternary amido acids. They should generally include an alkyl or alkenyl group of 7 to 18 carbon atoms.

Suitable amphoteric surfactants include simple betaines and sulphobetaine.

One or more nonionic surfactants may also be used in the cleansing composition of the present invention. Nonionic surfactants are preferably used at levels as low as 0.5, 1, 1.5 or 2 wt % and at levels as high as 6, 8, 10 or 12 wt % depending on the type of the cleansing composition. The nonionics which may be used include in particular the reaction products of compounds having a hydrophobic group and a reactive hydrogen atom, for example aliphatic alcohols, acids, amides or alkylphenols with alkylene oxides, especially ethylene oxide either alone or with propylene oxide. Specific nonionic detergent compounds are alkyl ($C_6$-$C_{22}$) phenols ethylene oxide condensates, the condensation products of aliphatic ($C_8$-$C_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxide, and the like.

Preferred nonionic surfactants include fatty acid/alcohol ethoxylates and sugar amide.

Polyol

Preferred cleansing compositions also include 3 to 40 wt % polyol. More preferred compositions may include 8 to 40 wt % polyols and still more preferred compositions include 25 to 35 wt % polyol.

Preferred polyols include maltitol, sorbitol, ethylene glycol, poly(ethylene glycol), propylene glycol, glycerol and higher alkoxylated derivatives of Polyhydric alcohols, such as propylene glycol, may serve as diluents. Other polyhydric alcohols such as glycerol may also serve as a humectant and moisturizer. A mixture of polyols is usually used. Especially preferred is a mixture of PEG, propylene glycol and sorbitol.

Water

Some formats may contain water. The amount of water will vary depending on the type of the composition. Some compositions may also be anhydrous. In addition, preferred compositions may include 0 to 15 w % optional ingredients such as perfumes; sequestering agents, such as tetrasodium ethylenediaminetetraacetate (EDTA), EHDP or mixtures in an amount of 0.01 to 1%, preferably 0.01 to 0.05%; and soluble coloring agents, and the like; all of which are useful in enhancing the appearance or cosmetic properties of the product.

The compositions may further comprise known antimicrobials such as 2-hydroxy-4,2',4' trichlorodiphenylether (DP300); preservatives such as dimethyloldimethylhydantoin (Glydant XL1000), parabens, sorbic acid and the like.

The compositions may also comprise coconut acyl mono- or diethanol amides as suds boosters, and strongly ionizing salts such as sodium chloride and sodium sulfate may also be used to advantage. Preferably strongly ionizing salts, otherwise known as electrolytes, will be present at less than 3, 2 or 1 wt %.

Antioxidants such as, for example, butylated hydroxytoluene (BHT) and the like may be used advantageously in amounts of about 0.01 wt % or higher if appropriate.

Water Soluble/Dispersible Polymers

Preferred water-soluble or water-dispersible polymer can be a cationic, anionic, amphoteric or nonionic polymer with molecular weight higher than 100,000 Dalton. These polymers are known to enhance in-use and after-use skin sensory feels, to enhance lather creaminess and lather stability, and to increase the viscosity of liquid cleanser compositions. Examples of water soluble or water-dispersible polymers include the carbohydrate gums such as cellulose gum, microcrystalline cellulose, cellulose gel, hydroxyethyl cellulose, hydroxypropyl cellulose, sodium carboxymethylcellulose, hydroxymethyl or carboxymethyl cellulose, methyl cellulose, ethyl cellulose, guar gum, gum karaya, gum tragacanth, gum arabic, gum acacia, gum agar, xanthan gum and mixtures thereof; modified and nonmodified starch granules with gelatinization temperature between 30 to 85° C. and pregelatinized cold water soluble starch; polyacrylates; alkaline soluble emulsion polymer such as ACULYN® 28, ACULYN® 22 or CARBOPOL® Aqua SF1; cationic polymer such as modified polysaccharides including cationic guar available from Rhone Poulenc under the trade name JAGUAR® C13S, JAGUAR® C14S, JAGUAR® 017, or JAGUAR® 016; cationic modified cellulose such as UCARE® Polymer JR 30 or JR 40 from Amerchol; N-HANCE® 3000, N-HANCE® 3196, N-HANCE® GPX 215 or N-HANCE® GPX 196 from Hercules; synthetic cationic polymer such as MERQUAT® 100, MERQUAT® 280, MERQUAT® 281 and MERQUAT® 550 by Nalco; cationic starches, e.g., STALOK® 100, 200, 300 and 400 made by Staley Inc.; cationic galactomannans based on guar gum of GALACTASOL® 800 series by Henkel, Inc.; QUADROSOFT® Um-200; and POLYQUATERNIUM®-24.

Gel forming polymers such as modified or nonmodified starch granules, xanthan gum, CARBOPOL®series, alkaline-soluble emulsion polymers and cationic guar gum such as JAGUAR® C13S, and cationic modified cellulose such as UCARE® Polymer JR 30 or JR 40 are particularly preferred for this invention.

Optional Active Agents

Advantageously, active agents other than emollients defined above may be added to the cleansing composition in a safe and effective amount during formulation to treat the skin during the use of the product provided that they do not exceed solubility limits. Suitable active ingredients include those that are soluble in the aqueous phase. Suitable active agents may be advantageously selected from vitamins, anti-acne actives; anti-wrinkle, anti-skin atrophy and skin repair actives; skin barrier repair actives; non-steroidal cosmetic soothing actives; skin lightening actives; sunscreen actives; sebum stimulators; sebum inhibitors; anti-oxidants; protease inhibitors; skin tightening agents; desquamating enzyme enhancers; anti-glycation agents; topical anesthetics and the like.

Product Format and Packaging

The disclosed cleansing composition can be in any format of cleansing compositions. Preferred formats include creams, lotion, gel or bar compositions intended for topical application to the skin. Specific known product formats include bodywash liquids, liquid cleansers for handwash, shampoo, bodywash gels, personal cleansing bars and aqueous self-foamable personal cleansing compositions. Appropriate packaging can be chosen to pack the products. Particularly preferred product formats include bodywash liquids and self-foaming personal cleansing compositions.

Self-foaming compositions are gradually becoming popular because the products are highly sustainable. A user needs much less water to rinse his hands as compared to the amount of water he would need to rinse of the lather from a bar or soap or a liquid soap. Therefore this format is considered to be highly sustainable format. Such compositions are packaged in special packs which allow air to be entrained (or aeration) of the product as it is dispensed for use. Such packages are widely available in markets.

Other Aspects:

In accordance with a second aspect is disclosed a method of cleansing the human body comprising the steps of:

(i) contacting the body, or any part thereof with a composition of the first aspect;

(ii) rubbing the composition on the body or the part thereof to generate foam; and (iii) rinsing off the composition.

In accordance with a third aspect is disclosed use of the composition of the first aspect for providing mild cleansing with antibacterial action.

In a fourth aspect is disclosed a method for providing mild cleansing with antibacterial action comprising step of using a composition of the first aspect.

The invention will now be explained with reference to non-limiting examples.

EXAMPLES

Example 1

Antibacterial Activity of a Preferred Cleansing Composition

Two preferred foaming cleansing compositions for hand wash were prepared for testing. Details of the composition are in table 1.

TABLE 1

| Ingredients | Composition 1 Wt % | Composition 2 Wt % |
| --- | --- | --- |
| Potassium cocoyl glycinate [30%] | 15.0 | 15.0 |
| Sodium lauroamphoacetate [30%] | 4.0 | 4.0 |
| Propylene glycol | 1.5 | 1.5 |
| Glycerin | 4.0 | 4.0 |
| Potassium hydroxide | 0.1 | 0.1 |
| Terpineol | 0.4 | 0.1 |
| Thymol | 0.1 | 0.2 |
| Water | Balance to 100% | Balance to 100% |

The basic bactericidal activity of the composition was determined by the standard EN 1040 method. It describes a suspension-based, quantitative, microbiology lab test for establishing the capability of a product to produce a reduction in the number of viable bacterial cells of relevant microorganisms under conditions defined by the standard. A test suspension of bacterial cells is added to a prepared sample of the test substance diluted with sterile deionised water. At the specified contact time, an aliquot is taken and the bactericidal and/or bacteriostatic activity is immediately suppressed by dilution or filtration neutralization. The number of surviving bacteria in each sample is determined standard culture plating techniques and the reduction in viable counts is calculated.

A brief description of the procedure is as follows:

About $10^7$ bacterial cells (*E. coli* ATCC 10536) were taken in a test tube and contacted with 50% diluted composition of Example 1 (and the other comparative compositions for a period of 15 seconds. The bacteria were taken out after 15 seconds of contact and the viable cells were counted by serial dilution and plating on agar plates. The data is presented in log (viable *E. coli*) which is the $\log_{10}$ of the number of viable *E. coli* remaining after 15 seconds of contact. Thus if $10^4$ bacteria remained, log (viable *E. coli*) is 4.

Zein Number—Procedure

The procedure followed herein is based on the one reported in E. Gotte, Skin Compatibility of Tensides Measured by Their Capacity for Dissolving Zein Protein, Proc. IV International Congress of Surface Active Substances, Brussels, 1964, pp 83-90.

This method involves measuring the solubility of Zein (corn protein) in cleansing compositions as follows:

5% of zein powder was stirred in 1% solution of the product at 35° C. for one hour. The mixture was centrifuged at 3000 rpm for 10 minutes. The solution was filtered to remove any un-dissolved zein powder. The amount of solubilized zein was determined by measuring Nitrogen content of the filtrate by micro Kjeldahl method. This estimate is then converted to calculate milligrams of Nitrogen estimated per gram of the product. This is referred to as the Zein number and indicates the amount of Zein dissolved by the surfactants in the cleansing composition per gram of the product.

The greater the zein score, harsher is the cleansing composition. The data on zein numbers is also shown in table 2 so as to make the table 2 comprehensive.

TABLE 2

| Composition tested | pH | Log reduction of viable bacteria at the end of | | | Zein number |
|---|---|---|---|---|---|
| | | 10 seconds | 30 seconds | 60 seconds | |
| Composition 1 | 9.5 | 4.5 | 6.9 | 7.6 | 22 |
| Composition 2 | 9.5 | 2.8 | 3.8 | 5.1 | 22 |
| Comparative Example 1 | 9.5 | 2.7 | 3.4 | 4.4 | 20 |
| Comparative Example 2 | 9.0 | 2.8 | 2.5 | 2.8 | 20 |
| Marketed product 1 | 10 | 1.2 | 3.8 | — | 390 |
| Marketed product 2 | 10 | 0.8 | 4.6 | 6.2 | 430 |

Note:
The Comparative Example 1 contained no antibacterial agent; balance of the composition same as Composition 1.
The Comparative Example 2 contained no antibacterial agent; balance of the composition same as Composition 1 but pH was fixed at 9 by reducing the alkali
Marketed product 1 was a commercial antibacterial bar of soap containing Trichlorocarbanilide and PCMX
Marketed product 2 was a commercial antibacterial bar of soap containing Trichlorocarbanilide.

The data in table 2 clearly indicates that the preferred Composition 1 shows high antibacterial activity even after the very short period of 10 seconds and this activity continues to increase sharply. However the Zein value is very low which is indicative of the mildness of the product. Composition 2, though having significantly lower antibacterial agents, showed high initial antibacterial action which also sustained for 60 seconds.

Comparative products (Comparative Example 1/Comparative Example 2) show good initial antibacterial activity but the activity tapers off at the end of 60 seconds.

The comparative Marketed product 1 and Marketed product 2 fail on two counts. First, inspite of the presence of known antibacterial agents, the soap bars did not provide appreciable log reduction. Further, but as expected, the soap bars showed very high Zein numbers which is indicative of the fact that the compositions are not mild to the skin.

While this invention has been described with respect to particular embodiments thereof, it is apparent that numerous other forms and modifications of the invention will be obvious to those skilled in the art. The appended claims and this invention generally should be construed to cover all such obvious forms and modifications which are within the true spirit and scope of the present invention.

The invention claimed is:

1. A cleansing composition comprising:
   (i) a non-soap surfactant which is an alkyl glycinate, alkyl carboxy glycinate, sarcosinate, glutamate or a mixture thereof; and,
   (ii) one or more antimicrobial agent, wherein said antimicrobial agent is thymol or terpineol or a mixture thereof,
   wherein pH of said composition is at least 8.5 and zein number of said composition is in the range of 10 to 65 and wherein soap content of said composition is not greater than 5 wt %.

2. A cleansing composition as claimed in claim 1 wherein said composition comprises an amphoacetate co-surfactant.

3. A cleansing composition as claimed in claim 1 wherein said composition comprises 1 to 20 wt % alkyl glycinate or alkyl carboxy glycinate.

4. A cleansing composition as claimed in claim 2 wherein said composition comprises 0.1 to 10 wt % amphoacetate co-surfactant.

5. A composition according to claim 1 comprising an emollient.

6. A composition as claimed in claim 5 wherein said emollient is selected from glycerin, alkylene glycol or a mixture thereof.

7. A method of cleansing the human body comprising the steps of:
   (i) contacting the body, or any part thereof with a composition as claimed in claim 1;
   (ii) rubbing the composition on the body or the part thereof to generate foam; and
   (iii) rinsing off the composition.

8. A method for providing mild cleansing with antibacterial action comprising a step of using a cleansing composition as claimed in claim 1.

* * * * *